(12) United States Patent
Li (10) Patent No.: US 10,232,074 B2
(45) Date of Patent: *Mar. 19, 2019

(54) SCENTED ELECTRONIC CANDLE DEVICE

(71) Applicant: Xiaofeng Li, Shenzhen (CN)

(72) Inventor: Xiaofeng Li, Shenzhen (CN)

( * ) Notice: Subject to any disclaimer, the term of this patent is extended or adjusted under 35 U.S.C. 154(b) by 24 days.

This patent is subject to a terminal disclaimer.

(21) Appl. No.: 15/451,351

(22) Filed: Mar. 6, 2017

(65) Prior Publication Data

US 2017/0368219 A1 Dec. 28, 2017

Related U.S. Application Data

(63) Continuation of application No. 15/207,411, filed on Jul. 11, 2016, now Pat. No. 9,585,980.

(30) Foreign Application Priority Data

Jun. 27, 2016 (CN) .......................... 2016 1 0478347

(51) Int. Cl.
*F21S 6/00* (2006.01)
*A61L 9/03* (2006.01)
(Continued)

(52) U.S. Cl.
CPC .............. *A61L 9/037* (2013.01); *A61L 9/032* (2013.01); *C11C 5/00* (2013.01); *C11C 5/008* (2013.01);
(Continued)

(58) Field of Classification Search
None
See application file for complete search history.

(56) References Cited

U.S. PATENT DOCUMENTS

| 6,491,516 B1 | 12/2002 | Tal |
| 2005/0007779 A1 | 1/2005 | Nozawa |

(Continued)

FOREIGN PATENT DOCUMENTS

| CN | 201093300 Y | 7/2008 |
| CN | 204268356 U | 4/2015 |

(Continued)

OTHER PUBLICATIONS

German Office Action issued for German Patent Application No. 102016008225.9, dated Dec. 19, 2016.
(Continued)

*Primary Examiner* — Elmito Breval
(74) *Attorney, Agent, or Firm* — Perkins Coie LLP (57) ABSTRACT

Scented electronic candle devices are described that facilitate operation and usage of a variety of features such as light or scent or movement of the flame, or a combination thereof. The disclosed features also include multiple settings for the variety of features. For instance, the scent feature can be activated or deactivated by multiple switches, remote, sensors, timers, or similar devices. In addition, the intensity of the scent features can be increased or decreased by increasing or decreasing the amount of heat or air. Similarly the light feature can be activated, deactivated, or set on a timer. Additionally, the scented electronic candle devices can be equipped with rechargeable batteries that can be charged using a wireless charging station or by connecting the scented electronic candle device to an electrical wall outlet.

15 Claims, 9 Drawing Sheets

(51) Int. Cl.
- *F21S 10/04* (2006.01)
- *F21S 9/02* (2006.01)
- *C11C 5/00* (2006.01)

(52) U.S. Cl.
CPC ............... *F21S 6/001* (2013.01); *F21S 9/02* (2013.01); *F21S 10/046* (2013.01); *A61L 2209/111* (2013.01); *A61L 2209/12* (2013.01); *A61L 2209/135* (2013.01)

(56) References Cited

U.S. PATENT DOCUMENTS

| | | |
|---|---|---|
| 2006/0192503 A1 | 8/2006 | Trombetta |
| 2007/0114969 A1* | 5/2007 | Marmaropoulos ... H02J 7/0027 320/108 |
| 2008/0129226 A1* | 6/2008 | DeWitt ............... H05B 37/029 315/307 |
| 2008/0151571 A1 | 6/2008 | Chen |
| 2010/0207538 A1 | 8/2010 | Chen |
| 2011/0000666 A1 | 1/2011 | Couto |
| 2011/0195787 A1 | 8/2011 | Wells |
| 2012/0093491 A1 | 4/2012 | Browder et al. |
| 2014/0035483 A1 | 2/2014 | Becker |
| 2014/0140042 A1 | 5/2014 | Scrreiber |
| 2014/0286024 A1 | 6/2014 | Li |
| 2014/0268652 A1 | 9/2014 | Li |
| 2015/0070874 A1 | 3/2015 | Beesley |
| 2016/0029461 A1 | 1/2016 | Noh et al. |
| 2016/0057829 A1 | 2/2016 | Li |

FOREIGN PATENT DOCUMENTS

| | | |
|---|---|---|
| DE | 212011100014 U1 | 4/2012 |
| DE | 202015000490 U1 | 3/2013 |
| DE | 202013012047 U1 | 2/2015 |
| DE | 202015102274 U1 | 5/2015 |
| EP | 1639291 B1 | 5/2009 |
| GB | 2267746 A | 12/1993 |
| GB | 2443926 A | 5/2008 |
| GB | 2527626 A | 12/2015 |
| WO | WO2012099718 A1 | 7/2012 |
| WO | WO2013020439 A1 | 2/2013 |
| WO | WO2014139483 A1 | 9/2014 |
| WO | WO2016000517 A1 | 1/2016 |

OTHER PUBLICATIONS

Canadian Examination Report issued for Canadian Patent Application No. 2930099, dated Jan. 5, 2017.
Canadian Examination Report issued for Canadian Patent Application No. 2930099, dated Aug. 15, 2016.
Combined Search and Examination Report in British Patent Application No. 1613387.8, dated Sep. 9, 2016.
Canadian Examination Report issued for Canadian Patent Application No. 2936225, dated Sep. 29, 2016.
German Office Action issued for German Patent Application No. 102016008825.7, dated Mar. 20, 2017.
Combined Search and Examination Report in British Patent Application No. 1613393.6, dated Sep. 9, 2016.

\* cited by examiner

SCENTED ELECTRONIC CANDLE DEVICE

RELATED APPLICATIONS

This patent document is a continuation of U.S. patent application Ser. No. 15/207,411 filed Jul. 11, 2016, which application claims priority to the Chinese patent application no. CN201610478347.6 filed on Jun. 27, 2016. The entire contents of the before mentioned Chinese patent application is incorporated by reference in this patent document.

FIELD OF INVENTION

The subject matter of this patent document relates to imitation candle devices, and more particularly, imitation candle devices that include scent producing features and components.

BACKGROUND

Traditional scented candles, when lit, provide a pleasant aroma in places such as homes, hotels, businesses, etc., The use of traditional scented candles, however, can be both hazardous and unappealing for several reasons. For example, a traditional scented candle effectively releases its fragrance only when its wick is lit. Lighting a traditional scented candle, however, can lead to risk of fire, damage to surface caused by hot wax, injuries suffered as a result of the hot wax or the flame, and possible emission of soot. A traditional scented candle can also be unappealing to a user who only wants to provide light to an area or to use the scent feature, but not both. As a result, scented electronic candles have become an increasingly popular alternative to traditional scented candles. Because scented electronic candles have no burning flame or hot wax, they are safer to use, especially around children. Further, scented electronic candles can incorporate a variety of features, such as light or scent, that can work independently or in combination. Such scented electronic candles can have a light source, a scent reservoir, and electronic circuits that control the operation of the scented electronic candle device.

SUMMARY OF CERTAIN EMBODIMENTS

The disclosed exemplary embodiments relate to scented electronic candle devices with enhanced features that facilitate the operations and various usages of those devices. The disclosed features enable a scented electronic candle device to safely and easily activate or deactivate features such as light or scent or movement of the flame. Other features also provide for an ease of operation. For example, a disclosed wireless charging feature can enable a scented electronic candle device to be conveniently placed and operated anywhere in a room. In addition, other disclosed features, such as sensors or timers, enable a scented electronic candle device to activate or deactivate various features such as light or scent or movement of the flame.

In an exemplary embodiment, a scented electronic candle device comprises a body with a top surface and a base, the top surface including an opening; a well structure placed in the opening of the top surface and movable in a vertical up or down direction within the opening, the well structure including an outer wall, an inner wall, and a floor and a top section that collectively form an enclosure for holding a scented material, wherein the top section of the well structure includes one or more openings, at least a section of the floor comprises a heat conducting material, and the well structure surrounds a central cavity; a flame assembly positioned within or below the cavity of the well structure and including a flame element that at least partially protrudes upwards from the cavity and from the top surface of the body; a thermal structure including one or more heater elements, the thermal structure thermally coupled to the well structure to provide thermal energy to the scented material of the reservoir and to enhance dissemination of the scented material from the enclosure to an outside environment through the one or more openings of the top section of the well structure; an electrical switch coupled to a power source to activate or deactivate at least the one or more heater elements; a support structure positioned below the well structure, the support structure mechanically coupled to both the well structure and to the electrical switch such that a vertical movement of the well structure causes activation or deactivation of the electrical switch. In an exemplary embodiment, the scented electronic candle device further comprising a barrel that covers the body and resembling an appearance of a wax material of a real candle.

In an exemplary embodiment, the scented material includes one or more of: a scented liquid, a scented gel, or a scented disk.

In an exemplary embodiment, the top section of the well structure is formed as a removable component that allows the top section to be removed and replaced.

In an exemplary embodiment, the flame assembly comprises a support element placed through a hole in the flame element to allow the flame element to be suspended within an interior of the flame assembly, and a magnetic coil positioned below the flame element and electrically connected to a printed circuit board to enable interactions between a magnetic field of the magnetic coil and a magnetic component of the flame element and to cause movements of the flame element in a manner that resembles movements of a real-life candle flame.

In an exemplary embodiment, a light source is positioned within an interior of the flame assembly and directed at an upward angle to illuminate the flame element from below.

In an exemplary embodiment, the flame element includes a light source.

In an exemplary embodiment, the one or more heater elements include a positive temperature coefficient materials.

In an exemplary embodiment, the flame element is stationary.

In an exemplary embodiment, the well structure is formed as a removable structure that is replaceably secured in a receptacle within the interior of the body.

In an exemplary embodiment, one or more rechargeable batteries is electrically connected to a printed circuit board.

In an exemplary embodiment, a mesh placed on top of the well structure to cover the one or more openings of the top section of the well structure.

In an exemplary embodiment, the electrical switch is further configured to activate or deactivate one or more of the following: a light source, a fan, an electromagnet, or all electrical components of the scented electronic candle device.

In an exemplary embodiment, a scented electronic candle system comprises an electric candle device that includes a body with a top surface and a base, the top surface including a partial opening that meets the top of a housing; a flame assembly positioned within the housing and including a flame element that at least partially protrudes from the top surface of the body, the top section of the flame assembly and the bottom section of the flame assembly each including a full or a partial opening; a baffle positioned below the bottom section of the flame assembly, the baffle including a central nozzle to direct passage of air from below the baffle to the flame assembly; a motorized fan positioned below the baffle, the motorized fan electrically connected to a printed circuit board; a scent container having a fully or partially open top section and positioned below the motorized fan such that an opening in the top section of the scent container is axially aligned with the central nozzle to allow, upon activation of the motorized fan, rapid diffusion of a scented material from the fully or partially open top section of the bottle to the central nozzle of the baffle to the interior of the flame assembly and to an outside environment of the electric candle device; and one or more rechargeable batteries and one or more charging coils located above the base and coupled to the rechargeable batteries; and a wireless charging base that is physically separate from the electric candle device and includes: a printed circuit board; and a coil electrically connected to the printed circuit board to receive an electrical current from the printed circuit board and to produce an electromagnetic field for wireless charging of the rechargeable batteries.

In an exemplary embodiment, the flame assembly comprises a support element placed through a hole in the flame element, the support element having two ends for pivotally suspending the flame element in the interior of the flame assembly and allowing the flame element to move upon receiving an air flow through the bottom section of the flame assembly.

An exemplary embodiment includes a wireless transceiver for receiving remote signals, wherein a speed or on-off activation of the motorized fan is controlled in response to a corresponding remote signal received by the transceiver.

In an exemplary embodiment, a speed or on-off activation of the motorized fan is controlled in response to reception of a remote control signal indicative of a blow of air.

In an exemplary embodiment, the scent container includes a wick.

In an exemplary embodiment, the scent container housing includes one or more notches to securely hold in place the scent container within one or more protrusions inside the body of the electric candle device.

In an exemplary embodiment, the scent container includes threaded grooves to securely hold in place the scent container within corresponding threads of inside the body of the electric candle device.

In an exemplary embodiment, a scented electronic candle device, comprises a back assembly including a primary printed circuit board electrically connected to electrical prongs of an electrical plug secured to the back assembly; a vertical plate with a back surface mechanically coupled to a front surface of the back assembly, the vertical plate including a scent bottle holder assembly mechanically coupled to the front surface of the vertical plate, wherein an inside surface of the scent bottle holder assembly includes one or more notches to securely hold in place a scent bottle with one or more protrusions; a wick positioned inside the scent bottle such that a top section of the wick is protruding out of the scent bottle and is in close proximity to one or more heater elements and a bottom section of the wick is inside the scented bottle, the wick dimensioned relative to an opening in the top of the scent bottle so a to provide a tight fit upon insertion of the wick into the scent bottle; a bracket cover including a top surface with a partial opening located above the wick to provide part of a pathway for scented air to propagate from the vicinity of the top section of the wick to an outside environment; a flame assembly positioned above the bracket cover inside the front shell, the flame assembly including a flame element and a light source, bottom and top sections of the flame assembly each including an opening that is axially aligned with the opening of the bracket cover and forming a part of the pathway for scented air to propagate from the vicinity of the top section of the wick to the outside environment; a top shell including a partial opening on top thereof, wherein the flame element protrudes at least partially from the partial opening on top of the top shell, the partial opening on top the top shell being axially aligned with the opening on the top section of the flame assembly and forming a part of the pathway for scented air to propagate from the vicinity of the top section of the wick to the outside environment.

In an exemplary embodiment, a front shell positioned on top of the scent bottle holder, the front shell including an opening that houses one or more sensors electrically connected to the primary printed circuit board.

In an exemplary embodiment, a secondary printed circuit board positioned within an interior space of the top shell and electrically coupled to the primary printed circuit board and to the light source.

In an exemplary embodiment, the electrical plug includes foldable electrical prongs that can be folded to be hidden from plain view.

In an exemplary embodiment, one or more switches are located on the back assembly, the one or more switches including a plurality of switch settings configured to control an operation of the one or more heater elements, thereby controlling a rate of evaporation of a scent from the wick.

In an exemplary embodiment, the flame assembly further comprises: a support element placed through a hole in the flame element, the support element having two ends for movably suspending the flame element within an interior space of the flame assembly; and a magnetic coil coupled to electronic circuits and located below the flame element to produce a magnetic field that interacts with a magnet on the flame element to cause the flame element to move in a manner that resembles the movement of a real-life candle flame.

DETAILED DESCRIPTION

In this patent document, the word "exemplary" is used to mean serving as an example, instance, or illustration. Any embodiment or design described herein as "exemplary" is not necessarily to be construed as preferred or advantageous over other embodiments or designs. Rather, use of the word exemplary is intended to present concepts in a concrete manner.

A scented electronic candle device can be designed to incorporate a variety of electrical and mechanical features that enable a safe and convenient operation of the scented electronic candle device. For example, scented electronic candle devices can be designed to offer features such as diffusing scent, providing light, wireless charging, or moving the flame. These features can be designed to operate independently or simultaneously. Another feature can be a sensor or a timer that can activate or deactivate various features. For some scented electronic candle devices, a protective mesh can also be placed on top of the scent container to protect against inadvertent spatter or spillage of the scented material. Thus, a variety of features can be incorporated into the scented electronic candle device that allow for a safe and convenient operation.

Figure 1:
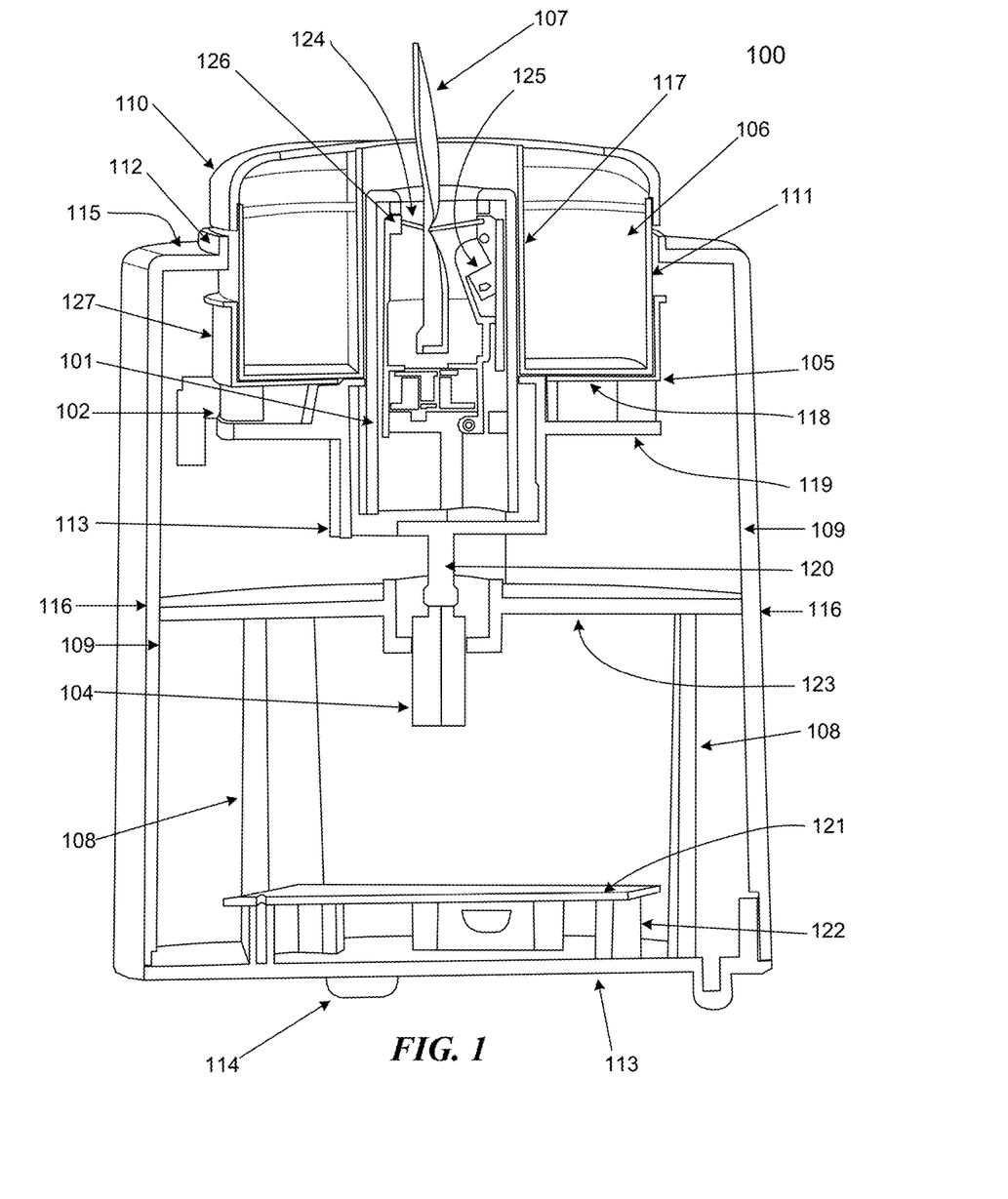
FIG. 1 illustrates a scented electronic candle device according to an exemplary embodiment.
Figure 4:
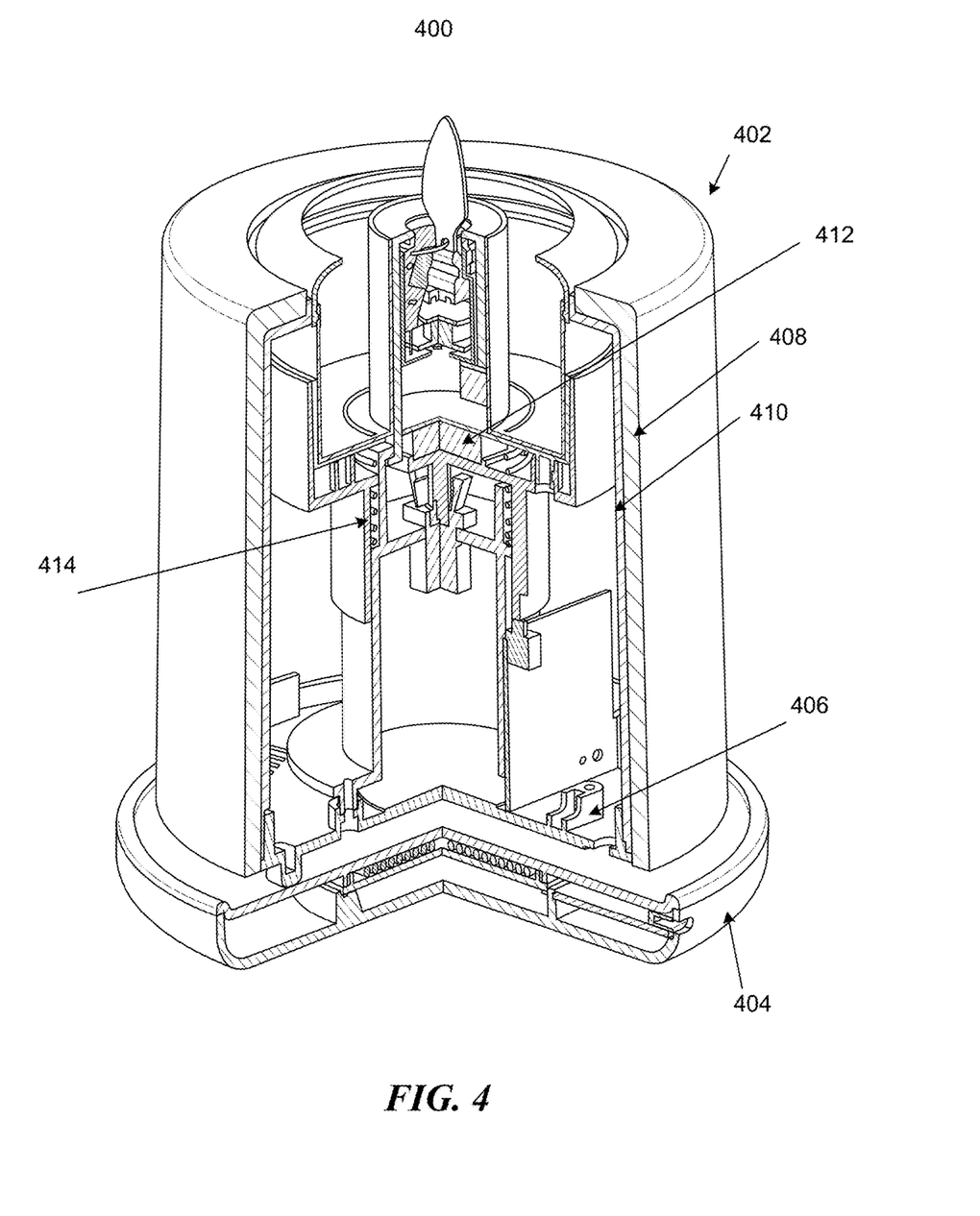
FIG. 4 illustrates a scented electronic candle device in conjunction with a wireless charging base according to an exemplary embodiment.

FIG. 1 illustrates a scented electronic candle device according to an exemplary embodiment. The exemplary scented electronic candle device 100 is designed to use heat to diffuse scented air. The scented electronic candle device 100 includes a wax barrel 116 that provides an appearance of a real wax candle (see also the outer barrel that is depicted in FIG. 4). The wax barrel 116 is positioned on the exterior of a cylindrical body 109 that provides an enclosure for housing the various components of the candle device 100. The wax barrel 116 has an inner diameter that is greater than the outer diameter of the cylindrical body 109. Thus in some embodiments, the wax barrel 116 can slide down the outside of the cylindrical body 109. The top surface 115 of the cylindrical body 109 has a circular opening with a circular edge 112 that protrudes slightly upwards. The wax barrel 116 can also include a corresponding top surface that is positioned on top of the top surface 115. The scented electronic candle device 100 also includes a base 113. The base 113 has multiple feet 114 that protrude outward and that allow the scented electronic candle device 100 to be placed on a surface. In one exemplary embodiment, the heights of the wax barrel 116 and the cylindrical body 109 can be substantially the same so that the wax barrel 116 covers the entire length of the cylindrical body 109. The wax barrel 116 can enable the scented electronic candle device 100 to have an aesthetic appearance. For example, wax barrels 116 with different colors and appearances can be manufactured and used to produce candles with different aesthetic appearances while maintaining the same design and components for the cylindrical body 109 and components therein. Alternatively, in some embodiments, the cylindrical body 109 includes an exterior wax-like surface that allows the cylindrical body 109 to have an aesthetic appearance, thus eliminating the need for the wax barrel 116.

As shown in FIG. 1, the upper section of the candle device 100 includes a well structure 106 that is located in an opening on the top of the scented electronic candle device 100. The well structure 106 can have a cylindrical (or doughnut-shaped structure or annulus-shaped) structure with a cavity in its center. In some embodiments, the well structure 106 is formed as an integral part of the candle device 100, while in other embodiments, the well-structure is formed as a replaceable component. The well structure 106 includes an outer circular wall 111, an inner circular wall 117, and a floor 118. The outer edge of the floor 118 meets the bottom of the outer circular wall 111, and the partial circular opening in the floor 118 meets the bottom of the inner circular wall 117. In the exemplary embodiment that is shown in FIG. 1, the length of the outer circular wall 111 is less than the length of the inner circular wall 117 so that the well structure 106 can have a slightly curved top. The volume that is formed between the outer circular wall 111 and the inner circular wall 117 is used to hold one or more scented materials. The well structure 106 is positioned around a flame assembly 101 and can slide up or down the flame assembly 101 as described below.

The well structure 106 is made of heat conducting material. A thermal structure 105 is positioned below the well structure 106 to provide thermal energy to the well structure 106 and the scented materials therein. The diameter of the outer circular wall 111 is less than the inner diameter of the circular edge 112 to allow the well structure 106 to slide up and down within the opening in the top surface 115. In an exemplary embodiment, the up and down movement of the well structure 106 can be used to activate the scent feature (described in greater detail below). In some embodiments, the well structure 106 can be removed and replaced with another well structure that, for example, holds another scented material. In some embodiments, when a user presses on the well structure or the scent block, the scent block will ascend so as to make it easier to be replaced. Once the scent block is replaced, pressing the scent block again makes the scent block to descend to a lower lever that allows the candle to operate in a normal fashion. The switching mechanism can automatically lock the scent block.

Alternatively, or additionally, in some embodiments, the top section 110 of the well structure 106 can be removed so as to allow replacement or replenishment of the scented materials within the cylindrical well structure 106. As shown in FIG. 1, the top section 110 can be curved to facilitate user's application of the pressure on the top section 110. The top section 110 can be formed using a heat-insulating material that can tolerate heat, so that a user will not burn his or her hand when pressing the top section 110. In an exemplary embodiment, the scented materials is a scented disk. In another exemplary embodiment, the scented materials may be a scented liquid. In yet another exemplary embodiment, the scented materials may be a combination of scented liquid and one or more scented disk(s).

The thermal structure 105 includes one or more heater elements 102 (e.g., including a positive temperature coefficient materials). The thermal structure 105 can be formed (or can include) a cylindrical structure having an open top and an outer cylindrical wall 127 to that forms a receptacle within the interior of the candle's body to receive the well structure 106. As shown in FIG. 1, the height of the outer cylindrical wall 127 is selected to allow sufficient clearance below the top surface 115 so as to allow the well structure 106 to slide up and down within the opening in the top surface 115. The floor 118 of the well structure 106 is thermally coupled to the thermal structure 105. In an exemplary embodiment, the thermal structure 105 includes protrusions (not shown) on the inside of the side wall that enable the thermal structure 105 to securely hold in place the well structure 106 that can have one or more notches (not shown) on the outside of the well structure 106. In some embodiments, the thermal structure 105 can also include one or more plates or surfaces to physically separate the well structure 106 from the heater elements 102 to prevent damage to the heater elements 102 (e.g., due to a user touching or pushing on the heater elements 102 when replacing the well structure 106), or to prevent damage to the well structure 106 itself as a result of excessive direct contact with the heater elements 102.

In some embodiment, the top section 110 of the well structure 106 is formed as an integrated part of the well structure 106, while in other embodiments, the top section 110 is a removable structure to facilitate replenishment or replacement of the scented materials. The well structure 106 can also include a mesh (not shown) that has a partial opening in the center and is positioned to cover the opening in the top section 110. Such a mesh or the membrane protects against inadvertent spatter or spillage of the one or more scented materials. In some embodiments, the mesh or the membrane can be made of a breathable film that covers at least part of the opening of the top section 110. The breathable film can would allow scent to be pass through as a gas, but prevents passage of liquid scent material.

Referring back to FIG. 1, the candle device 100 includes a flame element 107 that at least partially protrudes upward from the top section 110. The top of the flame assembly 101 can either be at the same level or below the top of an inner circular wall 117. The top of the flame assembly 101 has an opening in the center through which the flame element 107 protrudes upwards. The flame element 107 can include a hole (not shown) that allows a support element 124 to pass through the hole to suspend the flame element 107. The ends of the support element 124 are secured to the top of a flame support structure 126. In an exemplary embodiment, the flame element 107 can move to resemble the movement of a real-life candle flame. A magnetic coil (not shown) below the flame element 107 can interact with the magnet on the flame element 107 to cause the flame element 107 to move in a manner that resembles the movement of a real-life candle flame. The magnetic coil is electrically connected to a printed circuit board 121 that includes electronic circuits for energizing the magnetic coil with appropriate signals. In some exemplary embodiment, the flame element 107 is stationary, in which case, the support element 124 and the mechanism for movement the flame element 107 may not be needed.

The candle device 100 includes a light source 125 that is positioned within the cylindrical body 109 (e.g., within the flame support structure 126) so that the light source 125 shines light on the flame element 107. In another exemplary embodiment, the flame element 107 itself includes a light source (not shown) that is embedded within the upper (visible) section of the flame element 107. The light source is electrically connected to the printed circuit board 121.

As shown in FIG. 1, the candle device includes an elevation support or lift stand 103 has a cylindrical housing and a base. The elevation support or lift stand 103 also has one or more support structures 119 protruding outward from the exterior of the cylindrical housing to accommodate the placement of the one or more heater elements 102. The elevation support or lift stand 103 receives and holds in place the flame assembly 101. In an exemplary embodiment, the top section of the elevation support or lift stand 103 can also at least partially support the bottom of the well structure 106 or the bottom of the thermal structure 105, or both. The base of the elevation support or lift stand 103 contains one or more prongs 120 that receive one or more springs (not shown). The one or more prongs 120 are mechanically coupled to one or more electrical switches 104 via the one or more springs. The springs enable a user of the scented electronic candle device 100 to push the top section 110 of the well structure 106 to activate the one or more electrical switches 104. In an exemplary embodiment, the one or more electrical switches 104 turn on and off the scented electronic candle device 100, or a function thereof. For example, the one or more electrical switches 104 can activate or deactivated the light, the flame movement mechanism, the scent feature, or a combination thereof.

The one or more electrical switches 104 are mechanically secured to a fixing plate 123. The fixing plate 123 is secured on top of one of more long risers 108 that protrude upward from the base 113. The electrical contacts (not shown) of the one or more electrical switches 104 are electrically connected to the printed circuit board 121. The printed circuit board 121 is mechanically secured on top of one of more short risers 122 protruding upwards from the base 113. The printed circuit board 121 is connected to an electrical connector (not shown) that allows the printed circuit board 121 to receive power from an electrical outlet (not shown). In some embodiments, the printed circuit board can be additionally or alternatively powered by one or more rechargeable batteries.

FIGS. 2(A) to 2(D) illustrate a scented electronic candle device 200 with a wireless charging base 213 according to another exemplary embodiment. The exemplary scented electronic candle device 200 is designed to enable scent infused air to be drawn out of the scented electronic candle device 200. In addition, the exemplary scented electronic candle device 200 also includes a wireless charging base 213 that can charge the one or more rechargeable batteries 210 in the scented electronic candle device 200. The exemplary scented electronic candle device 200 includes a top surface 214, a body 204 (e.g. a cylindrical body), and a base 215. The base 215 can include one or more openings that allow air to be drawn into the candle device 200. The top surface 214 of the body 204 has a partial circular opening in the center that allows a flame element 201 (and a top protruding structure 219 of a flame assembly 202) to protrude upward and out of the top surface 214. The flame assembly 202 includes a cylindrical housing 203 in the form of an enclosure having a through hole on top thereof that allows the scented air to escape from within the candle device to an outside environment. The bottom of the cylindrical housing 203 has an opening to allow air to be drawn through the bottom opening into the housing 203 from within the scented candle device. Such an opening in the bottom of the housing can be a partial opening, or the cylindrical housing 203 can be a bottom-less structure.

Figure 2A:
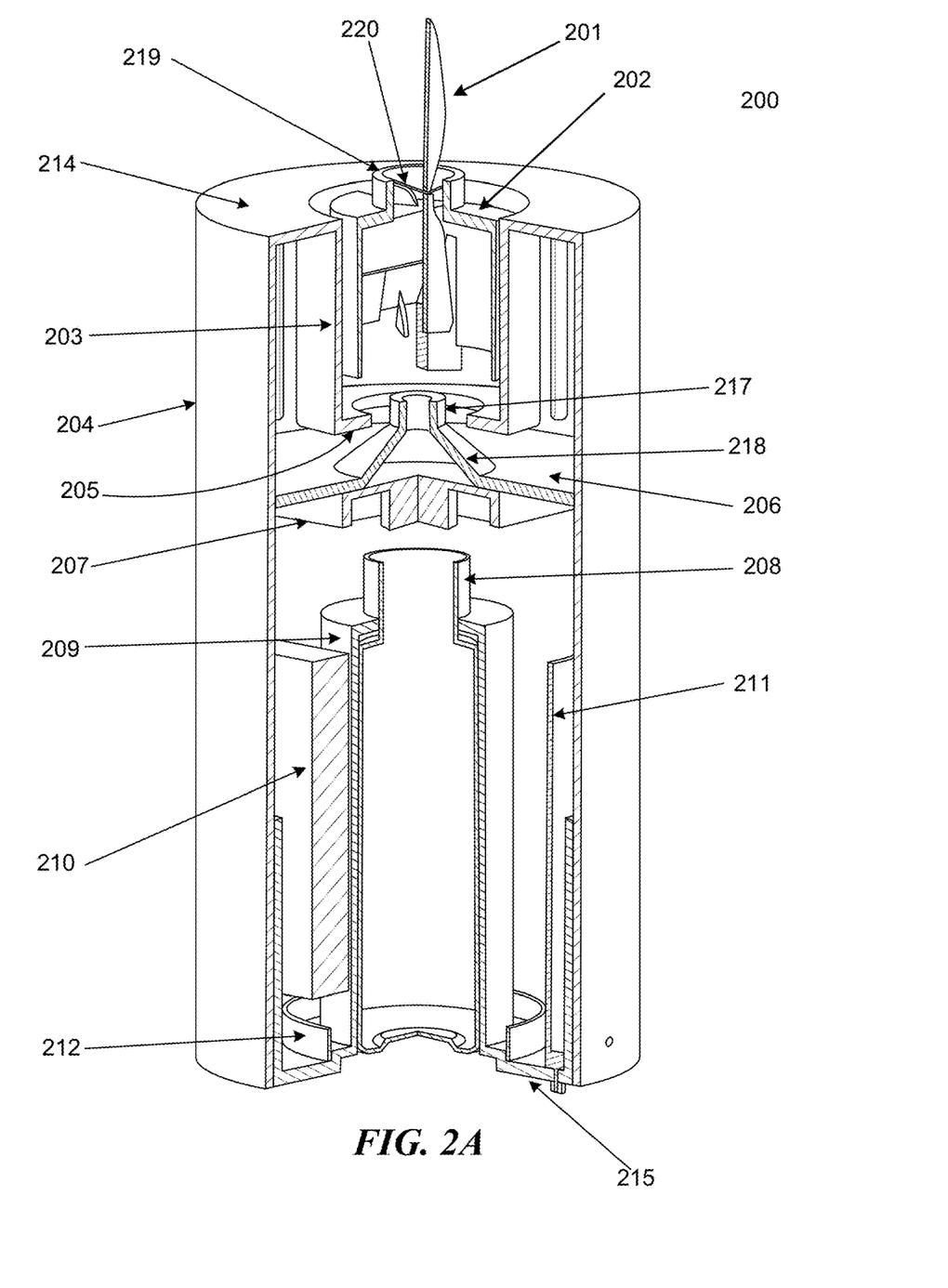
FIG. 2(A) illustrates a scented electronic candle device with a wireless charging base according to an exemplary embodiment.

In an exemplary embodiment, the flame element 201 can move to resemble the movement of a real-life candle flame. The flame element 201 can includes a hole (not shown) that allows a support element 220 to pass through the hole to suspend the flame element 201. The ends of the support element 220 are secured to the top protruding structure 219. The air drawn out of the scented electronic candle device 200 can cause the flame element 201 to move in a manner that resembles the movement of a real-life candle flame. In another exemplary embodiment, the flame element 201 includes a magnetic element and moves in response to a magnetic field of an electromagnet, as described in connection with FIG. 1. In another exemplary embodiment, the flame element 201 is stationary, in which case, the support element 220 may not be needed. The candle device 200 further includes a light source (not shown) that can shine light on the flame element 201. In some embodiments, the light is positioned in the flame assembly 202 and is positioned to illuminate the flame element 201 from within the candle device 200 through the opening on the top surface 214. In some exemplary embodiments, the flame element 201 includes a light source (not shown) embedded within the top section of the flame element 201 that is visible to a viewer. The light source is electrically connected to a printed circuit board 211.

Referring back to FIG. 2(A), the candle device 200 includes a baffle 206 located below the bottom surface 205 of the cylindrical housing 203. The baffle 206 has a circular outer edge that connects to an inclined region 218 that connects to a nozzle 217 in the center of the baffle 206. The nozzle 217 has an opening and protrudes upwards. The upward inclined region 218 of the baffle 206 meets the nozzle 217 on one side and the circular outer edge of the baffle 206 on the other side. The baffle 206 has an upside down funnel-like shape. The baffle 206 generally has an upward inclined shape that can help focus the air to move towards the flame assembly 202, and eventually out of the candle device 200. In some embodiments, the diameter of the nozzle 217 is less than or equal to the diameter of the opening in the bottom of the cylindrical housing 203 so that a motorized fan 207 can efficiently move the scent infused air from below the motorized fan 207 to flame assembly 202. The circular outer edge of the baffle 206 can be used to secure the baffle 206 to inner surface of the body 204. In the exemplary device of FIG. 2(A) the movement of air has the dual functionality of causing the movement of the flame element 201, as well as diffusing the scent to the outside environment through the same opening on top of the candle device 200. In some embodiments, the candle device 200 can include additional holes to facilitate dissimilation of the scent.

In FIG. 2(A), the motorized fan 207 is located below the baffle 206. The motorized fan 207 can be secured to the inner surface of the body 204. The motorized fan 207 has electrical contacts (not shown) that are electrically connected to the printed circuit board 211. When the motorized fan 207 is turned on, it can draw scent infused air out of the scented electronic candle device 200. The motorized fan 207 can be turned on or off by using a remote control device (not shown), one or more switches (not shown) located in the scented electronic candle device 200, one or more sensors (not shown) located in the scented electronic candle device 200, or a combination thereof. In an exemplary embodiment, a sensor (not shown) located in the scented electronic candle device 200 can turn on or off the motorized fan 207 when the sensor detects movement or the presence (or absence) of light. In another exemplary embodiment, the sensor can be a microphone (not shown) that can receive voice activation commands. In response to the voice activation commands, the electrical signals received by the microphone are converted into digital data, and analyzed to determine the contents of the voice commands using speech recognition techniques. Such signal processing operations can for, example be carried out, on a remote control device, such a smart phone, or a tablet that is equipped with a microphone. The voice commands can turn on and off the scent feature or the light feature, or any other included feature.

In another exemplary embodiment, the sensor can detect a blow on the candle. For example, a sensor (e.g., the microphone) can turn off the light source or the scent feature or both when the sensor detects a blow on the candle, or on the remote control device. In another exemplary embodiment, when the sensor detects a long or a strong blow on the candle, the sensor can diffuse more scent by increasing the speed of the motorized fan, and when the sensor detect short or a weak blow, it can cause a decrease in the speed of the motorized fan. The increase or decrease of fan speed in this scenario can be accompanied by a change in light's illumination intensity or illumination pattern.

While the above features related to remote control and blow detection have been described in the exemplary context of the candle device in FIG. 2A, it is understood that similar features can be implemented in other disclosed candle embodiments. For example, in another exemplary embodiment where scent diffusion is facilitated by using a heating element, when the sensor detects a long blow on the candle, the sensor can diffuse more scent by increasing the heat generated by the heat conducting material, or by flickering the light, or both. In another exemplary embodiment, the signals from a remote device can control the rate of heat dissipation (an thus scent diffusion) in a continuous or step-wise fashion. Other features and functionalities of the imitation candle device, such as operation of a timer features (e.g., 1 hour, 2 hour, etc. timed operation) can be implemented and controlled via control mechanisms on the candle device, or via a remote signal. In some embodiments, the candle includes a light sensor, which can detect ambient light. Based on such detection, the candle can be configured to, for example, operate when the ambient light is below a particular threshold (e.g., when it is night time). The candle, or a particular feature of the candle (e.g., scent feature) can be automatically turn on, an remain on while the ambient illumination is below the threshold. Additionally, or alternatively, the feature can be turn off automatically based on a timer setting (e.g., after 2 hours).

Referring back to FIG. 2A, the cylindrical scent bottle housing 209 extends inwards towards the motorized fan 207. The top of the cylindrical scent bottle housing 209 has a circular partial opening so that the top portion of a scent bottle 208 can pass through the partial opening on top of the cylindrical scent bottle housing 209 when the scent bottle 208 is fully inserted into the base 215. Thus, the outside diameter of the top portion of the scent bottle 208 is less than the diameter of the circular partial opening on top of the cylindrical scent bottle housing 209 so that the scent bottle 208 is prevented from touching or hitting the motorized fan 207. Other than the top portion of the scent bottle 208, the rest of the cylindrical portion of the scent bottle 208 has an outer diameter that is less than the inner diameter of the cylindrical scent bottle housing 209 so that the scent bottle 208 can be easily inserted into the cylindrical scent bottle housing 209.

In an exemplary embodiment, when the scent bottle 208 is fully inserted into the cylindrical scent bottle housing 209, the bottom of the scent bottle 208 may be positioned at the same level as the base 215.

In an exemplary embodiment, the scent bottle 208 may contain scented materials such as a scented liquid. In another exemplary embodiment, the scent bottle 208 may contain a wick (not shown) inserted into the scented materials such as a scented liquid.

A gap exists between top of the cylindrical scent bottle housing 209 and the bottom of the motorized fan 207 so that the top of the fully inserted scent bottle 208 is positioned below the bottom of the motorized fan 207. As a result, the motorized fan 207 can draw the scented air from scent bottle 208 through the nozzle 217, through the flame assembly 202, and out of the scented electronic candle device 200.

The scent bottle 208 can be inserted into and secured to a scent bottle housing 209. In an exemplary embodiment, the scent bottle 208 can be secured to the scent bottle housing 209 by having threaded grooves (not shown) into an inner portion of the scent bottle housing 209 and by having a corresponding threaded grooves (not shown) into the outer portion of the scent bottle 208. In another exemplary embodiment, the scent bottle 208 can be secured to the scent bottle housing 209 by having one or more notches (not shown) on the inside of the scent bottle housing 209 and by having one or more protrusions (not shown) on the outside of the scent bottle 208. In yet another exemplary embodiment, the scent bottle 208 can be secured to the scent bottle housing 209 using a combination of threaded grooves and one or more notches and protrusions.

One or more rechargeable batteries 210 can be installed in candle device in, for example, the space between the outer surface of the scent bottle housing 209 and the inner surface of the body 204. The one or more rechargeable batteries 210 can be secured to the either the outer surface of the scent bottle housing 209 or the inner surface of the body 204. The electrical contacts (not shown) of the one or more rechargeable batteries 210 are electrically connected to a printed circuit board 211.

The one or more rechargeable batteries 210 are positioned above the base 215 so that there is a gap between the bottom of the one or more rechargeable batteries and the base 215. One or more charging coils 212 are installed in the bottom section of the candle device 200 in the vicinity of the base 215 to allows wireless charging of the rechargeable batteries 210 when those charging coils 212 are placed in the electromagnetic field of a wireless charging base 213 (see FIGS. 2(B) to 2(D). In some embodiments, the charging coils are placed at a distance from the rechargeable batteries 210 to facilitate heat dissipation by the one or more charging coils 212 and the one or more rechargeable batteries 210. The electrical contacts (not shown) of the one or more charging coils 212 are electrically connected to a printed circuit board 211.

Figure 2B:
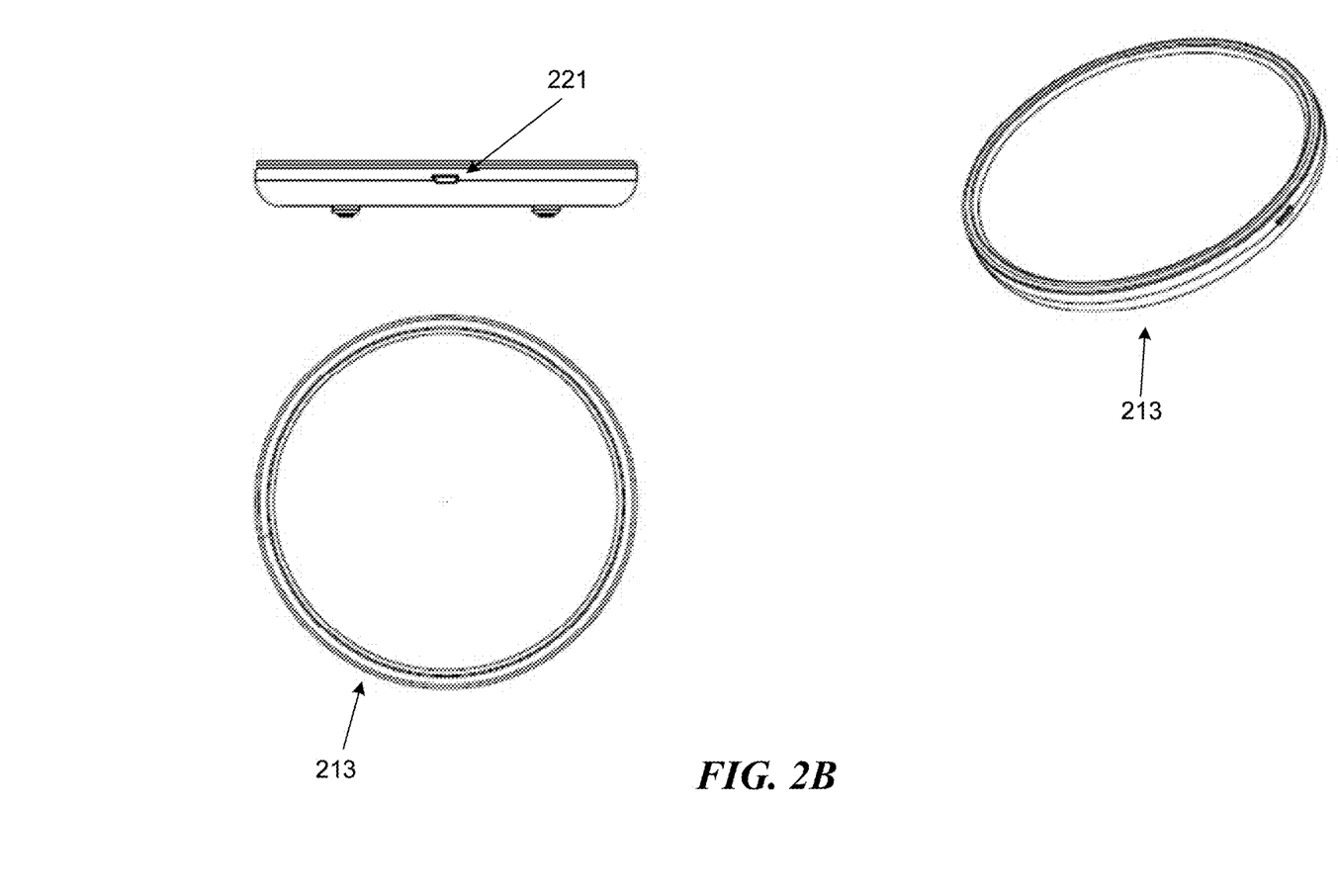
FIG. 2(B) illustrates a wireless charging base according to an exemplary embodiment.
Figure 2C:
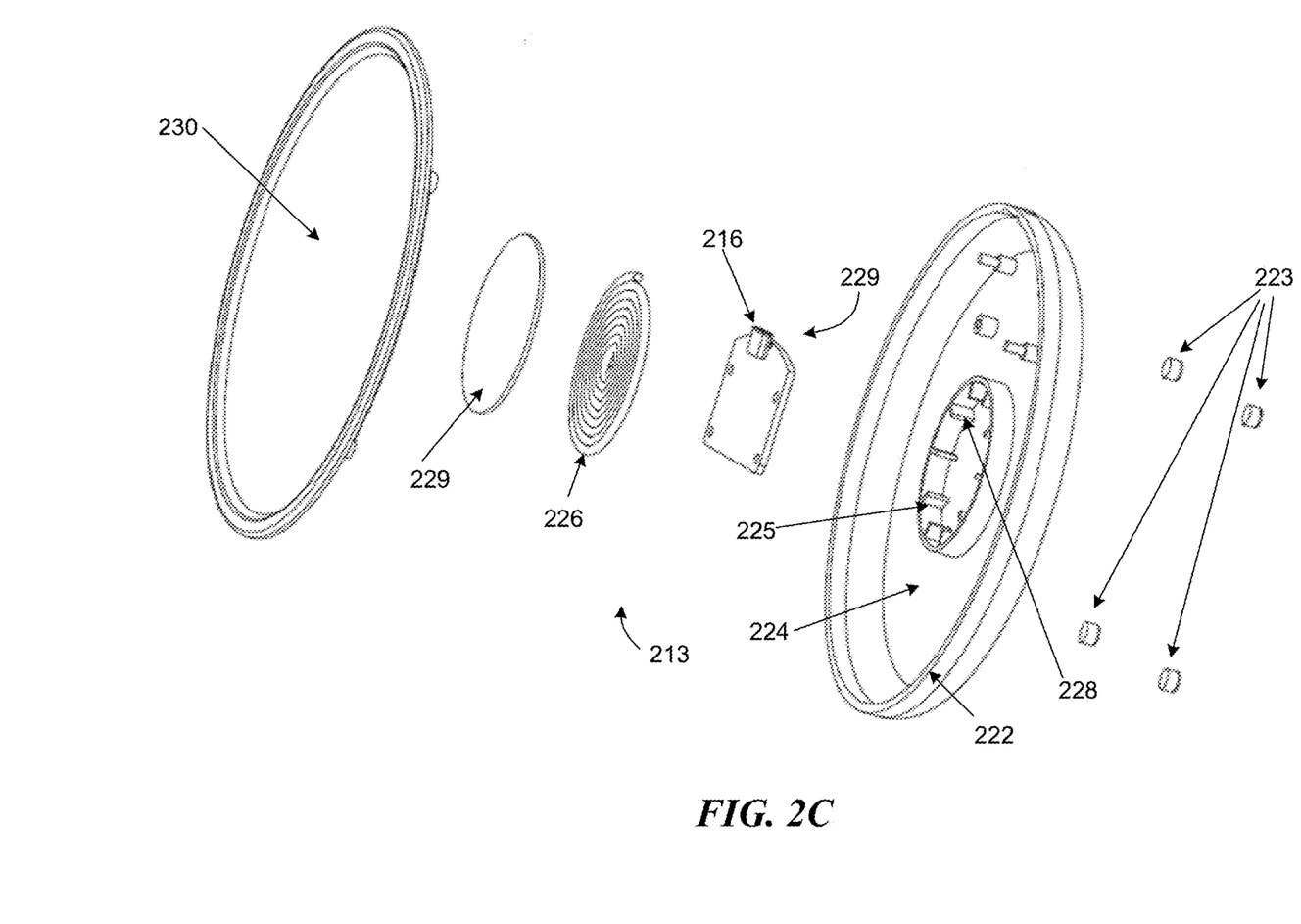
FIG. 2(C) illustrates an exploded view of a wireless charging base according to an exemplary embodiment.
Figure 2D:
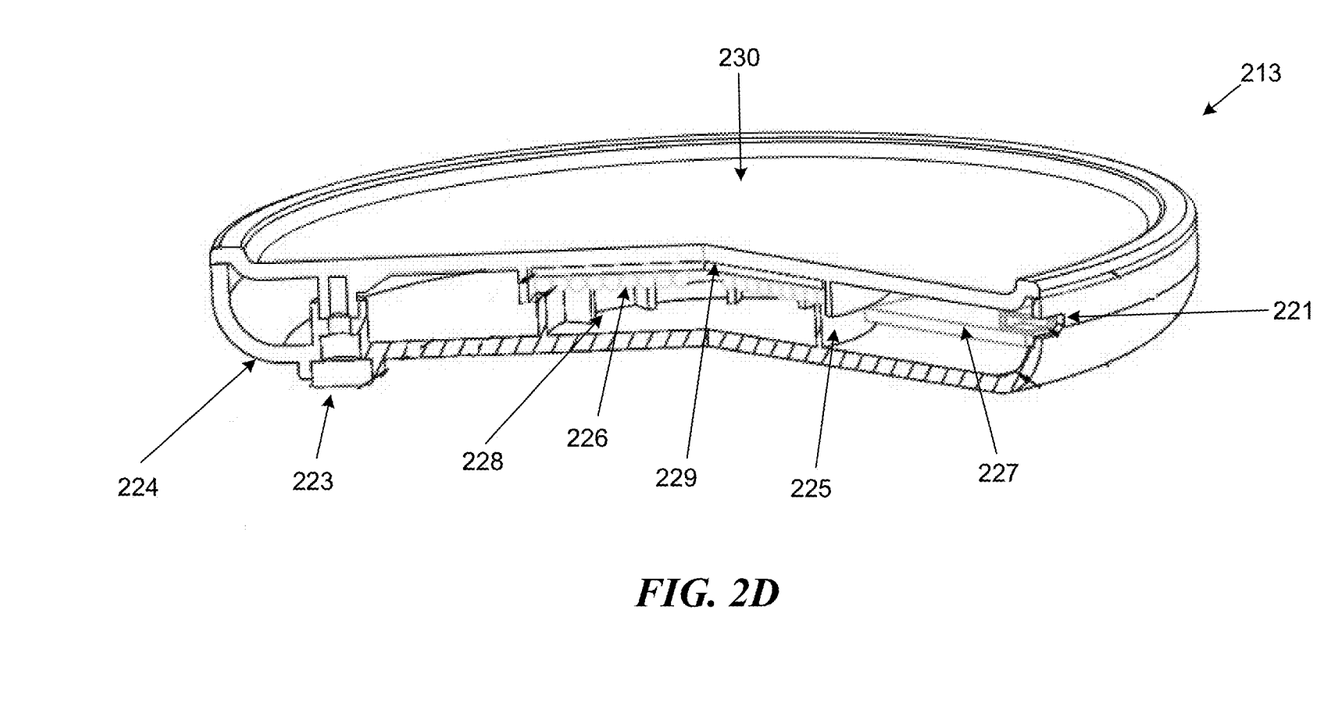
FIG. 2(D) illustrates a cutaway drawing of a wireless charging base according to an exemplary embodiment.

FIGS. 2(B) to 2(C) also illustrate different views of a wireless charging base 213 according to an exemplary embodiment. FIG. 2(D) also illustrates a cutaway drawing of a wireless charging base 213 according to an exemplary embodiment. The wireless charging base 213 includes an opening 221 that leads to a receptacle of an electrical connector 216, for example, a micro-B type USB female connector. The electrical connector 216 enables the wireless charging base 213 to be electrically connected to an electrical outlet (not shown) via an electrical plug (not shown) and an electrical cable (not shown). In an exemplary embodiment, the wireless charging base 213 can be circular. The wireless charging base 213 has a circular bottom shell 224 that is mechanically connected to the bottom of the cylindrical shell 222. Underneath the circular bottom shell 224 are multiple feet 223 that protrude outward and that allow the wireless charging base 213 to be placed on a surface. In the center of the top of the circular bottom shell 224 is a circular cylindrical ring 225 with partially protruding multiple spokes 228 interspersed around the inner edge of the circular cylindrical ring 225. The multiple spokes 228 begin on inner edge of the circular cylindrical ring 225 and partially protrude inward towards the center of the circular cylindrical ring 225. The heights of the circular cylindrical ring 225 and the multiple spokes 228 are less than the height of the cylindrical shell 222 so that additional elements such as the coil 226 and the insulation element 229 can be placed between the top shell 230 and the multiple spokes 228 and the circular cylindrical ring 225.

In an exemplary embodiment, a coil 226 is secured on top of riser structure such as a circular cylindrical ring 225 with the multiple spokes 228. A coil 226 can be placed on top of any other suitable structures. The coil 226 is electrically connected to a base printed circuit board 227. The base printed circuit board 227 is placed in the space between the cylindrical shell 222 and the circular cylindrical ring 225.

On top of the coil 226 is a circular insulation element 229. On top of the circular insulation element 229 is a top shell 230 that meets the top of the cylindrical shell 222.

When the scented electronic candle device 200 is placed near the top of the wireless charging base, 213, the wireless charging base 213 uses inductive or capacitive or any other wireless charging technique to charge the one or more rechargeable batteries 210 via the charging coils 212. The scented electronic candle device 200 can be placed on any compatible wireless charging base 213 to charge the one or more rechargeable batteries 210.

Figure 3A:
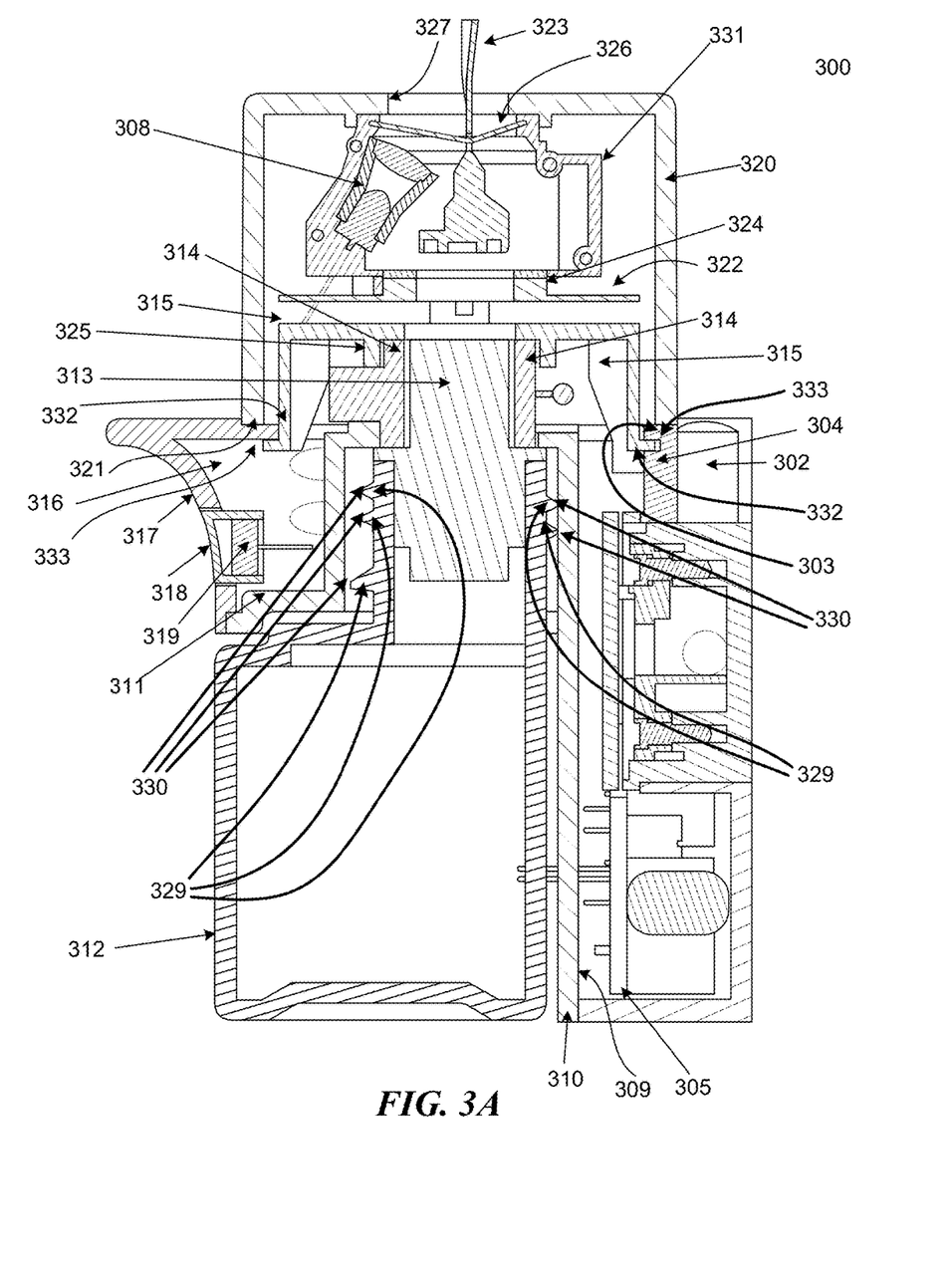
FIG. 3(A) illustrates a side view of a scented electronic candle device with an electrical plug according to an exemplary embodiment.
Figure 3B:
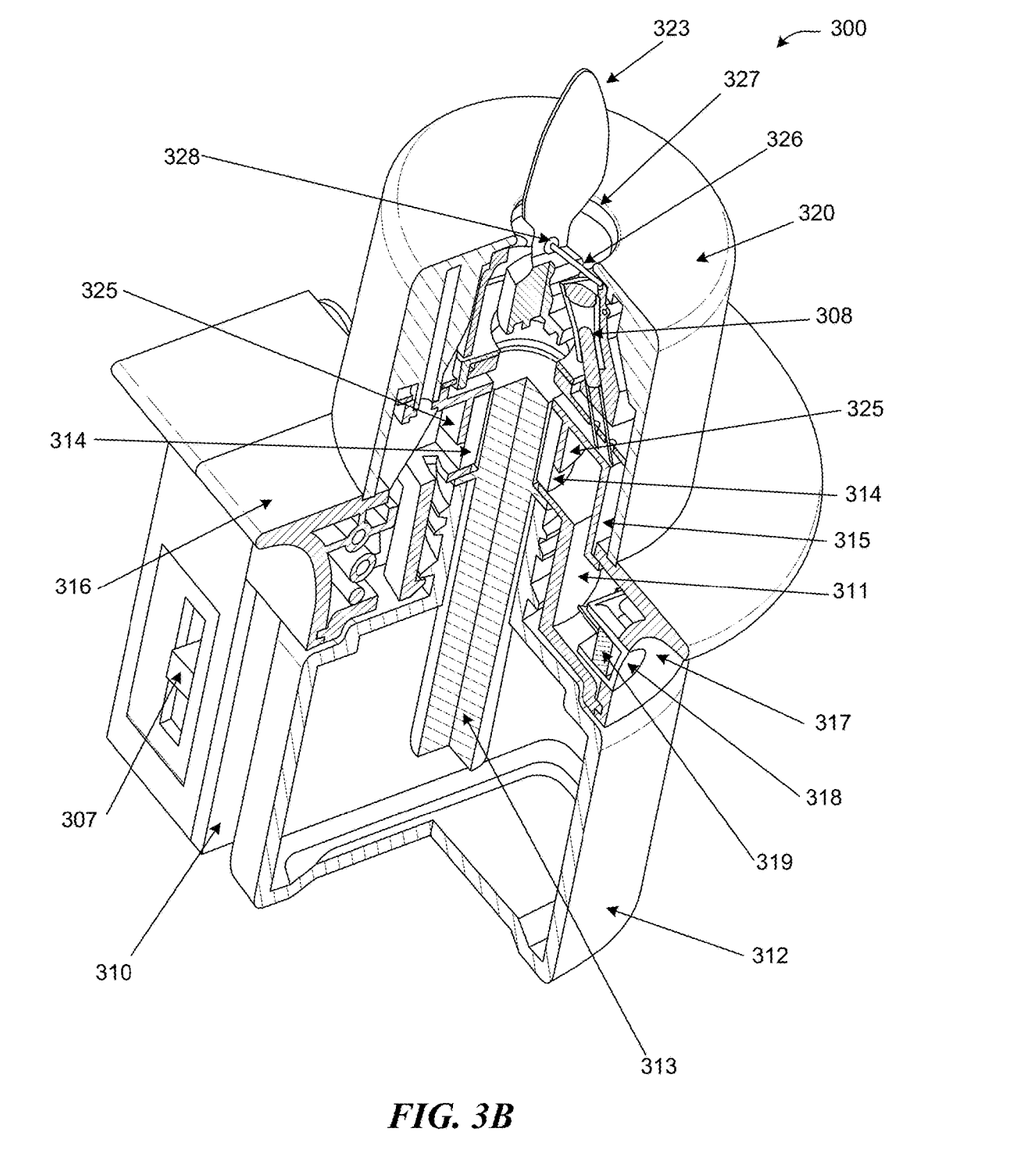
FIG. 3(B) illustrates a cutaway drawing of a scented electronic candle device with an electrical plug according to an exemplary embodiment.
Figure 3C:
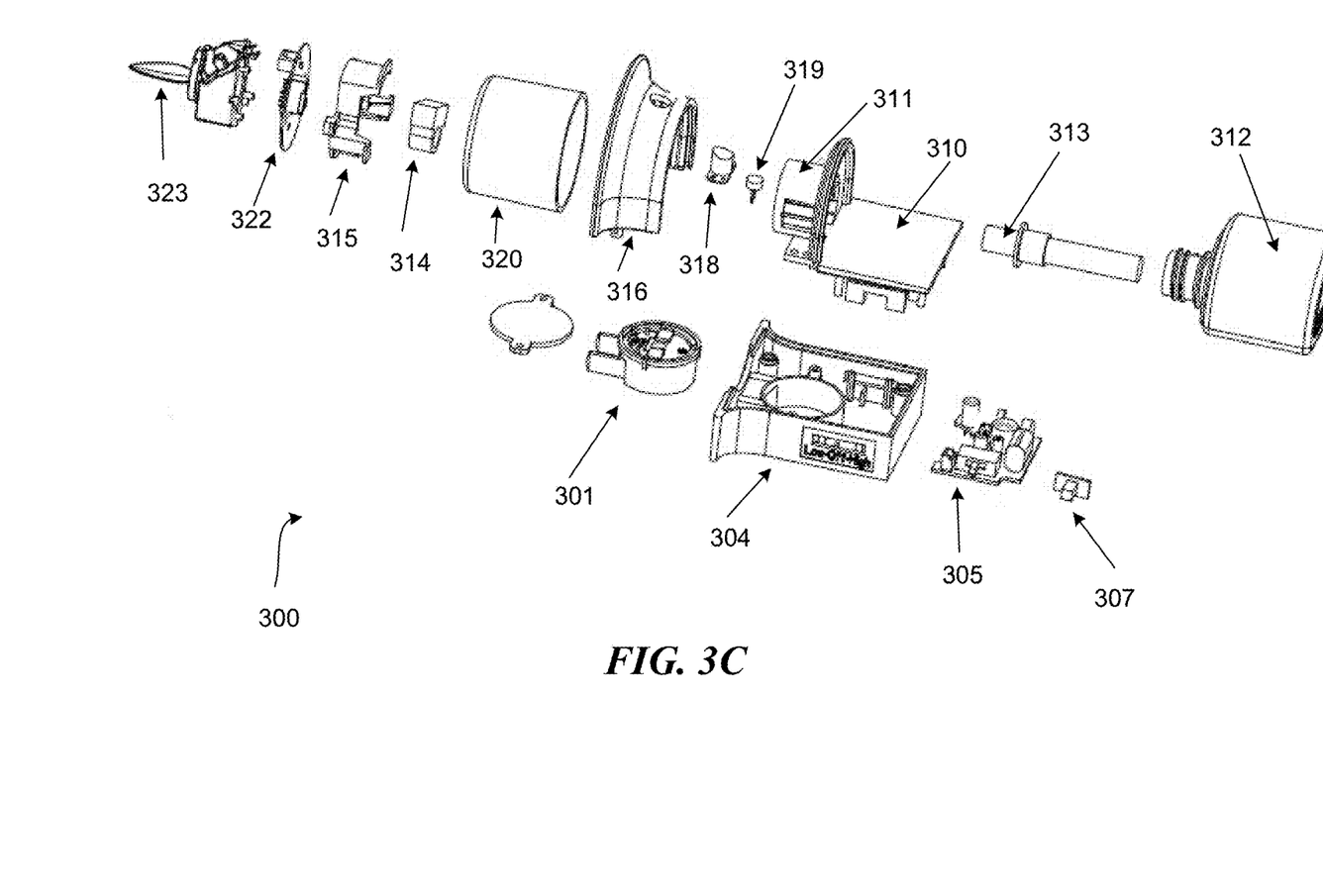
FIG. 3(C) illustrates an exploded view of a scented electronic candle device with an electrical plug according to an exemplary embodiment.

FIGS. 3(A) to 3(C) illustrate a scented electronic candle device 300 with an electrical plug 301 according to another exemplary embodiment. The exemplary scented electronic candle device 300 can use heat to diffuse scented air. Another feature of the exemplary scented electronic candle device 300 is an electrical plug 301 that is part of the scented electronic candle device 300. The exemplary scented electronic candle device 300 includes a back assembly 304, an electrical plug 301, a vertical plate 310, a scent bottle holder assembly 311, a front shell 316, and a top shell 320.

The electrical plug 301 is placed within and secured to the back assembly 304. The primary printed circuit board 305 is mechanically secured to the bottom of the back assembly 304. The electrical plug 301 has electrical prongs that are electrically connected to the primary printed circuit board 305. In an exemplary embodiment, the electrical plug 301 has foldable electrical prongs that can be folded in a recess of the back assembly 304. The electrical prongs can be locked in unfolded position to allow the scented electronic candle device 300 to be plugged into a wall electrical socket (not shown). The electrical plug 301 has a mechanism to hold the electrical prongs in the folded and unfolded positions. The electrical prongs 302 in an exemplary embodiment can be designed for example to be used in outlets in North America.

In some embodiments, the scented electronic candle device 300 includes one or more rechargeable batteries (not shown) that supply power to the candle device 300 and to allow stand-alone operation of the device. The one or more rechargeable batteries can be located in back assembly 304, are connected to the primary printed circuit board 305, and can be charged while the candle device 300 is connected to an electric outlet.

In an exemplary embodiment, one or more electrical switches 307 (see FIG. 3(B)) are located on one or both sides of the back assembly 304. The one or more electrical switches 307 are electrically connected to the primary printed circuit board 305. The electrical switches 307 can have, for example, three settings: "High," "Low," and "Off" that can control the amount of scent diffused in the air by setting the heat setting of the heater elements 314 to different levels. In the exemplary configuration of FIG. 3(A), the heater element 314 is a cylindrical in shape surrounds a wick 25. Heating of the wick 313 that has soaked up the scented material enhances the diffusion of the scent. It should be noted that the wick 313 (as shown in FIG. 3(B)) is typically long enough to reach the bottom of the scent bottle 312.

In another exemplary embodiment, another electrical switch (not shown) with, for example, three settings: "On," "Off," and "5 Hour" corresponding to the intensity level of the light emitted from a light source 308 and a timer feature to turn off the light source 308 after a certain amount of time. In another exemplary embodiment, a remote (not shown) can activate the multiple settings for the light source and the scent features by wirelessly sending information to a corresponding receiver (not shown) located in the scented electronic candle device 300. The front surface 309 of the back assembly 304 is mechanically connected to the back surface of a vertical plate 310. The height and width of the vertical plate 310 allow the vertical plate 310 to electrically insulate the electrical plug 301, the primary printed circuit board 305, and related electrical components located in the back assembly 304.

A scent bottle holder assembly 311 is provided so that a scent bottle 312 can be securely inserted into the scent bottle holder assembly 311. When the scent bottle 312 is fully and securely inserted into the scent bottle holder assembly 311, the bottom of the scent bottle 312 is at the same level as the bottom of the vertical plate 310 and the bottom of the back assembly 304. In the exemplary configuration of FIGS. 3(A) and 3(B), one side of the scent bottle 312 is flat so that it can be positioned next to vertical plate 310. The scent bottle 312 has a semi-circular shape on the top and on the bottom.

In some exemplary embodiments, the scent bottle 312 can be securely inserted into the scent bottle holder assembly 311 by using one or more protrusions or ridges 329 on the exterior of the top semi-circular shape on the scent bottle 312. The inside cylindrical surface of the top of the scent bottle holder assembly 311 has corresponding one or more notches 330 to accept the one or more protrusions or ridges 329. The scent bottle holder assembly 311 allows a user to easily and securely replace an empty scent bottle 312. In an exemplary embodiment, the scent bottle 312 may contain scented materials such as a scented liquid.

In another exemplary embodiment, the scent bottle 312 may contain a wick 313 inserted into the scented materials such as a scented liquid. The wick 313 protrudes from the top of the scent bottle 312. When the scent bottle 312 is fully inserted into the scent bottle holder assembly 311, the wick 313 is in close proximity to one or more heater elements 314. The wick 313 can also be wedged between the top of the scent bottle 312 and one or more heater elements 314 to prevent against leaking of the scented liquid. The one or more heater elements 314 are electrically connected to the primary printed circuit board 305.

The one or more heater elements 314 can have one or more protrusions that extend outward. The width of the one or more protrusions enables a bracket cover 315 to be placed on top of the heater elements 314. The indentations on the bottom of the one or more protrusions can be used to securely place the one or more positive temperature coefficient materials or heater elements 314 on top of the scent bottle holder assembly 311. Similarly, the indentations on the top of the one or more protrusions can be used to securely place the one or more positive temperature coefficient materials or heater elements 314 below the one or more protrusions 325 that point downward from the bracket cover 315.

The bracket cover 315 has top surface with a partial circular opening in the center 324. The diameter of the partial circular opening of the bracket cover 315 is substantially the same as the diameter of the wick 313 to allow the wick to effectively diffuse the scent. The bottom of the bracket cover 315 has one or more protrusions 332 pointing outwards that can be used to secure the bracket cover 315 to the corresponding one or more indentations 333 on both the top of the proximal side of a front shell 316 and the inner surface top of the back assembly 304.

A front shell 316 can be placed on top of the scent bottle holder assembly 311. The front shell 316 can have a semi-circular shape and be secured to the back assembly 304, or the vertical plate 310, or both. The vertical and horizontal center of the front shell 316 can have an opening 317 that is covered with a translucent or transparent cover 318. One or more sensors 319 can be installed facing outward and behind the translucent or transparent cover 318 in the opening 317. The one or more sensors 319 can be a photodiode that can detect ambient light, heat, movements, and/or infrared signals from a remote control device. The back of the front shell 316 has one or more protrusions that can be used to secure the front shell 316 to one or more sides on the inside of the back assembly 304.

A top shell 320 with a circular opening on its bottom is positioned on top of the front shell 316 such that the outer diameter of the top shell 320 is slightly less than the diameter of circular recessed areas 321 and 303 on the front shell 316. The top shell 320 is designed to accommodate a flame assembly 331 therein; the flame assembly 331 that is positioned above a bracket 315. The bracket 315 has top surface with an opening in the center thereof. In an exemplary embodiment, the diameter of the opening 324 is selected such that the area of the opening 324 is substantially equal to the cross-sectional area of the top of the wick 313 to provide an efficient means for allowing the scent material absorbed by the wick 313 to emanate through the opening 324 and ultimately reach the environment outside of the candle device 330. The bracket 315 can also be used to secure a secondary printed circuit board 322 that can include, for example, a magnetic coil (not shown) and associated circuits for generation of a magnetic field that interacts with a magnet component on the flame element 323. The secondary printed circuit board 322 is electrically connected to the primary printed circuit board 305.

In some implementations, the wick 313 is dimensioned to provide a top fit to the opening at the top of the scent bottle 312 to provide a liquid tight seal. In some embodiments, the wick 313 includes a circumferential structure that protrudes radially outward from the wick 313. Upon insertion of the wick 313 into the scented bottle 312, the circumferential structure provides a stop mechanism that prevents the wick 313 from being further inserted into the scent bottle 312.

The flame assembly 331 has light source 308 and a flame element 323. On the top of the top shell 320 is an opening 327 that allows the flame element 323 to at least partially protrude up from the top of the top shell 320, and the scent from the wick 313 to reach the outside environment. In some exemplary embodiments, the flame element 323 can move to resemble the movement of a real-life candle flame. In such embodiment, the flame element 323 includes a hole 328 that allows a support element 326 to pass through the hole to suspend the flame element 323. The ends of the support element 326 are secured to the flame assembly 331. A magnetic coil (not shown) energized by the secondary printed circuit board produces time-varying magnetic fields that interacts with a magnet on the flame to cause the flame element 323 to move in a manner that resembles the movement of a real-life candle flame. In another exemplary embodiment, the flame element 323 is stationary, in which case, the support element 326 and the mechanism for movement the flame element 323 may not be needed. In the exemplary configuration of FIGS. 3(A) and 3(B), the flame assembly 331 houses a light source 308 that shines light on the flame element 323. The light source 308 is electrically connected to the secondary printed circuit board 322. In another exemplary embodiment, the light source 308 can be electrically connected to the primary printed circuit board 305. In some embodiments, the flame element 323, additionally or alternatively, includes a light source (not shown).

In an exemplary embodiment, the scented electronic candle device can activate or deactivated multiple features such as light, scent, flame movement, or a combination thereof. The scented electronic candle device can also have multiple settings associated with the multiple features. The multiple settings can be controlled by using, for example, multiple switches, remote, sensors, timers, or similar devices. In some embodiments, the scented candle includes a safety mechanism that causes the power supply shut down if the candle falls down or the scent compartment is tilted or is falling. The safety mechanism can, for example, be implemented using a sensor (e.g., a mercury or similar type switch, a gyro, an accelerometer, an optical sensor, etc. and associated circuitry) that detects a fall, a tilt or a movement of the candle (or the scent component) beyond a minimum threshold to produce a signal or a trigger. Upon detection of such a trigger, the power to the candle (or a sub-system of the candle) is turned off In some embodiments, the imitation candle device may exclude any kind of physical switches or switch mechanisms on the device, and solely operate in response to receiving signals from a remote device. Such signals are received by the appropriate receiving elements (e.g., infrared detector, Bluetooth receiver, etc.) of the imitation candle device. The received signals are processed by a processor (e.g., an MCU) to decode and obtain the command signals that are used to activate, deactivate, modulate or otherwise affect the operation of the desired feature.

In an exemplary embodiment, the scented electronic candle device can be refilled with or replaced by the same or another scented material. The scented materials can be one or more scented disk(s), a scented liquid, a combination of scented liquid and scented disks, or any other suitable scented materials.

In an exemplary embodiment, the scent feature of the scented electronic candle device can be activated by heating an area close to or in contact with the scent container or the wick of the scented container. In an exemplary embodiment, the scent feature of the scented electronic candle can be activated by drawing air out of the scented electronic candle device.

In an exemplary embodiment, the scented electronic candle device can be plugged into a wall electrical socket. The scented electronic candle device can have an electrical plug that has electrical prongs that can be folded away from plain view to allow stand-alone operation of the candle, and to facilitate storage of the candle device.

In an exemplary embodiment, the electrical plug can charge the one or more rechargeable batteries included in the scented electronic candle device. In an exemplary embodiment, the scented electronic candle device includes one or more rechargeable batteries that can be wirelessly charged using a wireless charging base.

FIG. 4 illustrates a scented electronic candle system 400 that includes a scented candle device 402 and a wireless charging base 404 that is positioned below the scented candle device 402 according to an exemplary embodiment. One of the features of the candle system 400 in FIG. 4 is the ability to include an electrical cord (not shown) for delivering power to the candle device 402. The wires of the cord can be connected to the connector 406, which allows power to be delivered to the candle device 402. The power cord can for example include an on-off switch that allows a user to turn off the candle without having to reach for an on-off switch that may reside at the bottom of the candle. The power cord can also allow recharging of the batteries, in some cases. This capability can be provided in addition to the wireless charging of the batteries. It should be noted that the candle system 400 includes certain combination of different elements that were previously discussed in connection with previous figures. For example, the candle device 402 includes an outer was shell 408, a cylindrical body 410, a heater element 412 and springs 414 that were described earlier. For instance, the springs 414 allows the top section of the candle device 402 to be pressed down to turn the candle and/or its scent feature on or off.

Some of the components of the exemplary embodiments described herein use terms such as circular, or semi-circular, or cylindrical, or well, or disk, or coil, or diameter to describe the shapes and associations between the various objects. Such descriptions, however, are not to be construed as limiting the full scope of the inventive features. For example, the shapes of the scented electronic candle device, the wireless charging base, and associated various objects in the scented electronic candle device and the wireless charging base can be a quadrilateral such as a square or a rectangle, or a polygon such as a triangle or a hexagon, or a polygon with one or more curved surfaces, or a closed curve such as an oval.

Some of the disclosed embodiments can be implemented as devices or modules using hardware circuits, software, or combinations thereof. For example, a hardware circuit implementation can include discrete analog and/or digital components that are, for example, integrated as part of a printed circuit board. Alternatively, or additionally, the disclosed components or modules can be implemented as an Application Specific Integrated Circuit (ASIC) and/or as a Field Programmable Gate Array (FPGA) device. Some implementations may additionally or alternatively include a digital signal processor (DSP) that is a specialized microprocessor with an architecture optimized for the operational needs of digital signal processing associated with the disclosed functionalities of this application. Similarly, the various components or sub-components within each module may be implemented in software, hardware or firmware. For example, the disclosed circuit boards can include a variety of digital, analog, optoelectronic, acousto-electric, memory and other components that allows reception, processing and/or transmission of signals to/from the imitation candle device, and enables selective control of various candle features. The connectivity between the modules and/or components within the modules may be provided using any one of the connectivity methods and media that is known in the art, including, but not limited to, communications over the Internet, wired, or wireless networks using the appropriate protocols.

The foregoing description of embodiments has been presented for purposes of illustration and description. The foregoing description is not intended to be exhaustive or to limit embodiments of the present invention to the precise form disclosed, and modifications and variations are possible in light of the above teachings or may be acquired from practice of various embodiments. The embodiments discussed herein were chosen and described in order to explain the principles and the nature of various embodiments and its practical application to enable one skilled in the art to utilize the present invention in various embodiments and with various modifications as are suited to the particular use contemplated. The features of the embodiments described herein may be combined in all possible combinations of methods, apparatus, modules, and systems.

In particular, in exemplary embodiments described in connection with the above figures, certain features of scented candles are described in exemplary configurations to facilitate understanding of the described features. It is understood, however, that different features can be combined or removed in additional embodiments. For example, an exemplary candle device can include both a fan and a magnetic mechanism for moving the flame element. As another example, an exemplary candle device can include a wick but not a heating element for diffusing the scent. Thus, the features, settings, and components described for one exemplary embodiment can be easily combined with or added to another exemplary embodiment by a person of ordinary skill in the art.

What is claimed is:

1. A scented electronic candle device, comprising:
    a body with a top surface and a base, the top surface including a partial opening;
    a flame assembly positioned in the body, the flame assembly includes a flame element that at least partially protrudes from the top surface of the body, and a top section of the flame assembly and a bottom section of the flame assembly each including an opening;
    a scent container having a fully or partially open top section and positioned below the bottom section of the flame assembly and aligned with the opening at the bottom section of the flame assembly to allow diffusion of a scented material from the fully or partially open top section of the scent container to the interior of the flame assembly and to an outside environment of the electric candle device; and
    one or more rechargeable batteries located above the base.

2. The scented electronic candle device of claim 1, wherein the scent container includes one or more notches to securely hold in place the scent container within one or more protrusions inside the body of the scented electronic candle device.

3. The scented electronic candle device of claim 1, wherein the scent container includes threaded grooves to securely hold in place the scent container within corresponding threads of inside the body of the scented electronic candle device.

4. The scented electronic candle device of claim 1, further comprising:
    a motorized fan positioned above the top section of the scent container and below the bottom section of the flame assembly, wherein the motorized fan is structured to draw air from one or more openings in the base of the scented electronic candle device to assist with diffusion of the scented material.

5. The scented electronic candle device of claim 4, further comprising a sensor to turn on or off the motorized fan in response to detection of (a) a movement or (b) detection of a presence or an absence of light.

6. The scented electronic candle device of claim 4, further comprising a wireless transceiver for receiving remote signals, wherein a speed or on-off activation of the motorized fan is controlled in response to a corresponding remote signal received by the transceiver.

7. The scented electronic candle device of claim 1, further comprising:
    one or more heater elements in close proximity to the scent container, wherein the one or more heater elements positioned in proximity of scent container to assist with diffusion of the scented material.

8. The scented electronic candle device of claim 7, wherein the one or more heater elements include a positive temperature coefficient material.

9. The scented electronic candle device of claim 7, further comprising one or more switches including a plurality of switch settings configured to control an operation of the one or more heater elements to control a rate of evaporation of a scent from the scent container.

10. The scented electronic candle device of claim 1, further comprising an electrical connector to electrically connect the scented electronic candle device to an electrical wall outlet and to allow recharging of the one of more rechargeable batteries.

11. The scented electronic candle device of claim 1, further comprising one or more charging coils located above the base and coupled to the one or more rechargeable batteries.

12. The scented electronic candle device of claim 1, wherein the flame assembly comprises a support element placed through a hole in the flame element, the support element having two ends for pivotally suspending the flame element in an interior of the flame assembly.

13. The scented electronic candle device of claim 1, further including a light source positioned within the flame assembly.

14. The scented electronic candle device of claim 13, wherein the flame element includes the light source.

15. The scented electronic candle device of claim 1, wherein the scent container includes a wick to assist with diffusion of the scented material.

* * * * *